United States Patent [19]

Spes et al.

[11] Patent Number: 5,442,025
[45] Date of Patent: Aug. 15, 1995

[54] ORGANOSILSESQUIOXANES HAVING AT LEAST ONE MESOGENIC SIDE GROUP

[75] Inventors: Peter Spes, Munich; Franz-Heinrich Kreuzer, Martinsried; Christian Freyer, Burghausen; Mechthild Hessling, Kirchheim b. München, all of Germany

[73] Assignee: Consortium für elektrochemische Industrie GmbH, Munich, Germany

[21] Appl. No.: 180,759

[22] Filed: Jan. 10, 1994

Related U.S. Application Data

[63] Continuation of Ser. No. 3,817, Jan. 11, 1993, abandoned, which is a continuation of Ser. No. 667,131, Mar. 11, 1991, abandoned.

[30] Foreign Application Priority Data

Mar. 14, 1990 [DE] Germany ............ 40 08 076.5

[51] Int. Cl.⁶ ............................................. C08G 77/26
[52] U.S. Cl. ........................................ 528/15; 528/31; 528/26; 528/27; 528/28; 528/29; 556/437; 556/462; 556/455; 525/479
[58] Field of Search ............... 528/31, 26, 27, 28, 528/29, 15; 525/479; 556/437, 462, 455

[56] References Cited

U.S. PATENT DOCUMENTS

| | | | |
|---|---|---|---|
| 3,000,858 | 9/1961 | Brown, Jr. | 525/477 |
| 3,615,272 | 10/1971 | Collins | 528/23 |
| 4,358,391 | 11/1982 | Finkelmann et al. | 252/299.01 |
| 4,388,453 | 6/1983 | Finkelmann et al. | 528/15 |
| 4,410,570 | 10/1983 | Kreuzer et al. | 427/374.1 |
| 4,826,943 | 5/1989 | Ito et al. | 528/21 |
| 5,039,771 | 8/1991 | Morimoto et al. | 528/14 |
| 5,047,492 | 9/1991 | Weidner et al. | 528/15 |
| 5,098,978 | 3/1992 | Riepl et al. | 528/15 |

FOREIGN PATENT DOCUMENTS

| | | |
|---|---|---|
| 0163495 | 12/1985 | European Pat. Off. . |
| 0291884 | 11/1988 | European Pat. Off. . |
| 0354753 | 2/1990 | European Pat. Off. . |

OTHER PUBLICATIONS

Chemical Abstracts vol. 98 81903v.
"Liquid Crystalline Silsesquioxanes" Franz-Heinrich Kreuzer et al. Macromol. Chem., Macromol. Symp. 50 215–228 (1991).
*Silicones Chemistry and Technology* pp. 100–101 1989.

*Primary Examiner*—Robert E. Sellers
*Assistant Examiner*—Margaret W. Glass
*Attorney, Agent, or Firm*—Martin Connaughton

[57] ABSTRACT

Organosilsesquioxanes having at least one mesogenic side group and processes for their preparation, which comprise reacting organosilsesquioxanes having at least one Si-bonded hydrogen atom with chiral or achiral mesogenic compounds containing an aliphatic multiple bond.

7 Claims, No Drawings

ORGANOSILSESQUIOXANES HAVING AT LEAST ONE MESOGENIC SIDE GROUP

This application is a continuation of application Ser. No. 08/003,817, filed Jan. 11, 1993, now abandoned, which application is a continuation of application Ser. No. 07/667,131, filed Mar. 11, 1991, now abandoned.

The invention relates to organosilsesquioxanes and more particularly to organosilsesquioxanes having at least one mesogenic side group. The invention also relates to processes for preparing organosilsesquioxanes having at least one mesogenic side chain and their use.

BACKGROUND OF THE INVENTION

Linear organopolysiloxanes modified by mesogenic groups are known and described for example, by H. Finkelmann, G. Rehage, Makromol. Chem., Rapid Commun., 1, 733 (1980), H. Ringsdorf, A. Schneller, Makromol. Chem., Rapid Commun., 3,557 (1982), G. W. Gray, D. Lacey, G. Nestor, M. S. White, Makromol. Chem., Rapid Commun., 7, 71 (1986), H. J. Coles, R. Simon, Mol. Cryst. Liq. Cryst., 102, 75 (1984), R. M. Richardson, N. J. Herring, Mol. Cryst. Liq. Cryst., 123, 143 (1985), H. Richard, M. Mauzac, H. T. Nguyen, G. Sigaud, M. F. Archard, F. Harduin, H. Gasparoux, Mol. Cryst. Liq. Cryst., 155, 141 (1988), H. Sackmann, H. Schubert, Z. Chem., 26, 66 (1986), V. P. Shibaev, N. A. Plate, Advances in Polymer Sciences, Springer Verlag, 60-61, 173 (1984), H. Zaschke, M. Krücke, M. Schlossarek, Acta Polymerica, 39, 607 (1988) and U.S. Pat. No. 4,358,391 (H. Finkelmann, Wacker-Chemie GmbH; published on 9th November 1982).

With these organopolysiloxanes, conversion into the liquid crystal orientated state often presents difficulties because relatively long conditioning times are required in order to achieve a high degree of order. Although shorter-chain species of the type mentioned above orientate themselves spontaneously, they usually have undesirable tacky properties.

Furthermore, U.S. Pat. No. 4,410,570 (F.-H. Kreuzer, Consortium für elektrochemische Industrie GmbH; published on 18th October 1983) describes cyclic organopolysiloxanes having at least one mesogenic group and European Published Specification 163,495 (To Imai, Toray Silicone Co. Ltd., published on 4th December 1985) describes non-crosslinked branched organopolysiloxanes having at least one mesogenic radical.

It is therefore an object of the present invention to provide organosilsesquioxanes having at least one mesogenic side group. Another object of the present invention is to provide a process for preparing organosilsesquioxanes having at least one mesogenic side group. Another object of the present invention is to provide organosilsesquioxanes containing a large number of mesogenic groups which have a wide variation in properties. A further object of the present invention is to provide organosilsesquioxanes having at least one mesogenic side group which have relatively high glass transition points. A still further object of the present invention is to provide organosilsesquioxanes having at least one mesogenic side group which are capable of being crosslinked.

SUMMARY OF THE INVENTION

The foregoing objects and others which will become apparent from the following description are accomplished in accordance with this invention, generally speaking, by providing organosilsesquioxanes having at least one mesogenic side group and a process for preparing the same which comprises reacting organosilsesquioxanes having at least one Si-bonded hydrogen atom with a chiral or achiral mesogenic compound containing an aliphatic multiple bond.

DESCRIPTION OF THE INVENTION

The organosilsesquioxanes of this invention having at least one mesogenic side group are preferably those of the general formula $$[R(SiR^1_2O)_aSiO_{3/2}]_x \qquad (I)$$

in which x is the number 4, 6, 8, 10 or 12, preferably 6, 8 or 10, and more preferably 8, a can be the same or different and is an integer of from 0 to 10, preferably from 0 to 3, and more preferably 0 to 1, $R^1$ represents the same or different monovalent organic radicals and R can be the same or different and represents a chiral or achiral mesogenic radical, with the proviso that up to x-1 of the R radicals can also be the same as $R^1$.

Although not shown in formula (I), all or some of the diorganosilyl groups $—(SiR^1_2)_a—$, in which a and $R^1$ are the same as above, can be replaced by other organosilicon radicals, such as, for example, cyclic or branched organ(poly)siloxane radicals.

The term "mesogenic groups" is well known to those skilled in the art. It is those groups which can give rise to liquid crystal properties in a molecule.

The mesogenic radicals represented by R can be all of the mesogenic groups known to date. Mesogenic groups are described, for example, in Dietrich Demus et al., "Flüssige Kristalle in Tabellen (Liquid Crystals in Tables)", VEB Deutsher Verlag für Grundstoffindustrie, Leipzig, Volume I (1974) and Volume II (1984).

Examples of mesogenic groups are derivatives of cyclohexane, such as cyclohexyl cyclohexylcarboxylate, phenyl cyclohexylcarboxylate, cyclohexyl phenyl ether, cyclohexylbenzenes, dicyclohexyl derivatives, derivatives of stilbene, cinnamic acid derivatives, such as for example cinnamic acid alkyl esters and cinnamic acid aryl esters, phenyl benzoate and its derivatives, steroids, such as cholesterol, derivatives thereof, such as cholesterol esters, cholestane and derivatives thereof, benzylidene anilines, azobenzene and its derivatives, azoxybenzene and derivatives thereof, alkyl and alkoxy derivatives of biphenyl and terphenyl, and Schiff's bases.

In the above formula, R preferably represents a radical of the formula

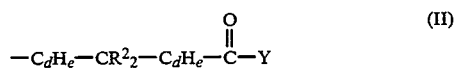
(II)

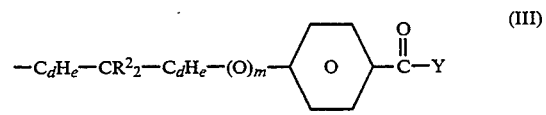
(III)

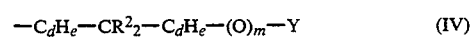
(IV)

or

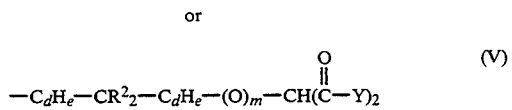
(V)

in which $R^2$ can be the same or different and represents a hydrogen atom, cyano group, hydroxyl group, halogen atom or alkyl group having from 1 to 4 carbon atoms, d represents in each case the same or different integers of from 0 to 12, preferably between 1 and 6, e represents in each case the same or different integers of from 0 to 24, preferably between 1 and 12, m is 0 or 1 and y represents the cholesteryl radical or a radical of the formula (VI), (VII), (VIII) or (IX).

The radical $R^2$ is preferably a hydrogen atom, hydroxyl group or fluorine, chlorine or bromine atom or the methyl or ethyl radical, with the hydrogen atom, fluorine atom and methyl group being the preferred radicals.

The radical Y can be a radical of the general formula

 (VI)

in which P can be the same or different and represents an oxygen atom, a sulfur atom, $-C_dH_e-$, where d and e are the same as above, or an N-alkylamino radical, preferably P is an oxygen atom, v can be the same or different and represents an integer between 0 and 12, preferably 0, 1 or 2, E can be the same or different and represents $-CH_2-CH_2-$, $-CH_2O-$, $-OCH_2-$, $-COS-$ or a conjugated multiple bond system between identical or different atoms, such as, for example, $-CH=CH-$, $-C\equiv C-$, $-CH=N-$ or $-N=N-$, r can be the same or different and represents an integer between 0 and 8, preferably between 0 and 2, and more preferably 1, c can be the same or different and represents an integer between 1 and 5, preferably between 1 and 2, f can be the same or different and represents an integer between 1 and 5, preferably between 1 and 2, $R^4$ is the same or different and represents a hydrogen atom, halogen atom, hydroxyl group, nitro group, amino group or cyano group or chiral or achiral hydrocarbon, hydrocarbonoxy, ester, acyl or acyloxy radicals, which can optionally be substituted, and B can be the same or different and represents a divalent cyclic radical selected from the group consisting of cyclic. hydrocarbons radicals and heterocyclic radicals, with the proviso that these radicals can be substituted by a halogen atom, hydroxyl group, nitro group, amino group or cyano group or by chiral or achiral hydrocarbon, hydrocarbonoxy, ester, acyl or acyloxy groups, which can optionally be substituted, preferably by a fluorine or chlorine atom, a cyano, hydroxyl, nitro, amino or dimethylamino group or methyl, methoxy, ethyl or ethoxy radicals.

Examples of radicals represented by $R^4$ are alkyl radicals, such as the methyl, ethyl, n-propyl, iso-propyl, 1-n-butyl, 2-n-butyl, isobutyl, tert-butyl, n-pentyl, iso-pentyl-, neo-pentyl- and tert-pentyl radical, hexyl radicals, such as the n-hexyl radical, heptyl radicals, such as the n-heptyl radical, octyl radicals, such as the n-octyl radical and iso-octyl radicals, such as the 2,2,4-trimethylpentyl radical, nonyl radicals, such as the n-nonyl radical, and decyl radicals, such as the n-decyl radical; cycloalkyl radicals, such as cyclopentyl, cyclohexyl and cycloheptyl radicals, methylcyclohexyl radicals and derivatives thereof substituted by halogen atoms and/or hydroxyl groups, and the corresponding alkoxy groups; alkenyl radicals, such as the vinyl and the allyl radical, aryl radicals, such as the phenyl radical and substituted phenyl radicals, and the corresponding aryloxy radicals.

Other examples of radicals represented by $R^4$ are substituted and unsubstituted alkyl or aryl esters, and aliphatic and aromatic carbonyl and oxycarbonyl groups, which can likewise be substituted.

Preferred radicals represented by $R^4$ are a hydrogen atom or cyano or nitro group and methyl, methoxy, ethyl and ethoxy radicals, as well as chiral and achiral oxycarbonyl groups and ester groups, the hydrogen atom, cyano group and methoxy group being particularly preferred.

Examples of the radical B are phenylene radicals, such as the 1,4-phenylene radical, cyclohexylene radicals, such as the 1,4-cyclohexylene radical, pyridinediyl, pyrimidinediyl, pyridazinediyl, triazinediyl, tetrazinediyl, dioxanediyl, tetrahydrofurandiyl, thiophenediyl, thiazolediyl, thiadiazolediyl, pyrrolediyl and pyrazolediyl radicals, epoxy groups and spiro compounds.

The radical Y can be a radical of the general formula

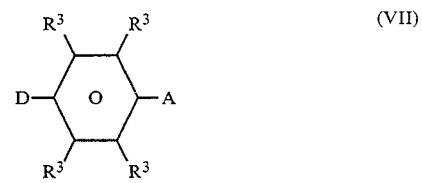 (VII)

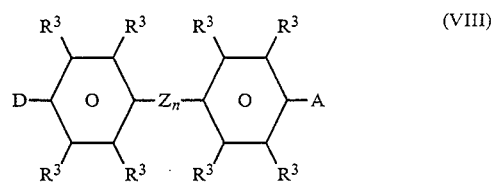 (VIII)

or

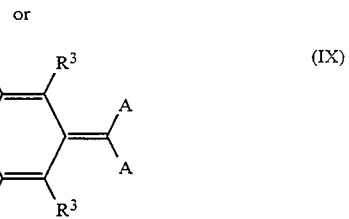 (IX)

in which $R^3$ can be the same or different and is the same as $R^4$, A can be the same or different and represents an electron-attracting radical, such as, for example, nitro, cyano, dicyanovinyl, tricyanovinyl, acyl, trifluoromethyl and alkoxysulfonyl groups, D can be the same or different and represents an electron-repelling radical, such as, for example, a halogen atom or amino, hydroxyl, mercapto, alkyl, alkoxy, alkylthio, acyloxy and vinyl groups, Z represents a conjugated multiple bond system between identical or different atoms, such as, for example, $-CH=CH-$, $-C\equiv C-$, $-CH=N-$ and $-N=N-$, and n is an integer of from 0 to 8, preferably between 0 and 2, and more preferably 1, with the proviso that one hydrogen atom in the radicals Y of the general formulas (VII) to (IX) is replaced by a chemical bond. Preferably, radical Y in the radical R is bonded via D, in which R and D are the same as above and in particular in the case where D is an amino or hydroxyl group.

Examples of $R^3$ radicals are the same as the examples mentioned for the $R^4$ radical.

Preferred radicals represented by $R^3$ are the hydrogen atom, fluorine and chlorine atom and cyano, hydroxyl, nitro, amino and dimethylamino group, as well as methyl, methoxy, ethyl and ethoxy radicals, in which the hydrogen atom, fluorine atom, chlorine atom and cyano group being particularly preferred.

Preferred radicals represented by D are amino, alkyl, alkoxy, alkylthio and acyloxy groups, with the amino and alkoxy groups being the preferred radicals.

The preferred meaning of Z is —CH=CH—, —CH=N— and —N=N—.

The radicals represented by Y are preferably radicals of the general formula (VI).

Examples of the radical R are

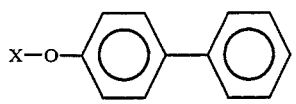

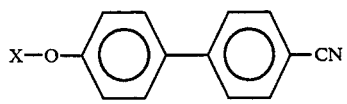

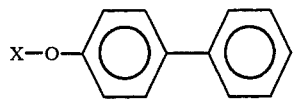

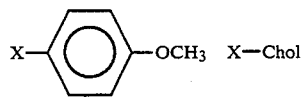

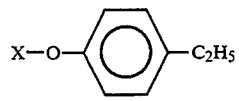

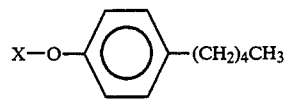

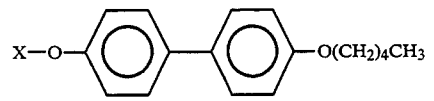

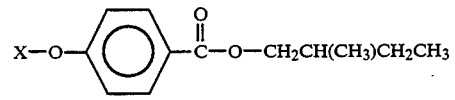

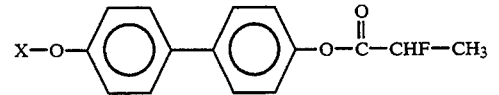

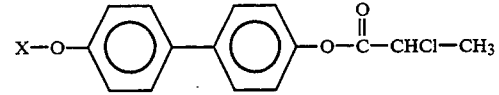

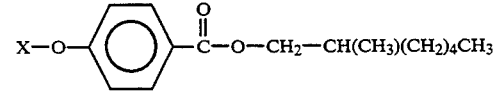

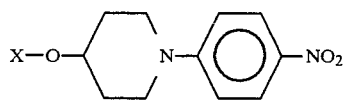
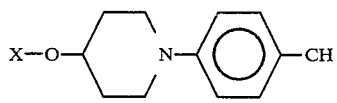
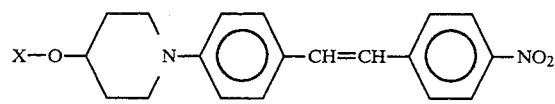
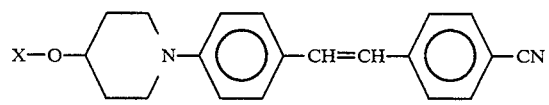
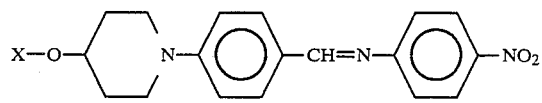
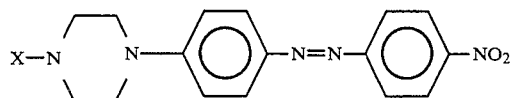
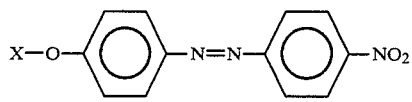
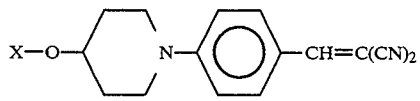
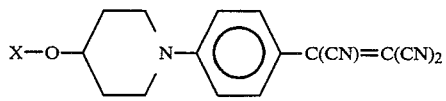
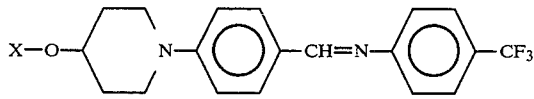
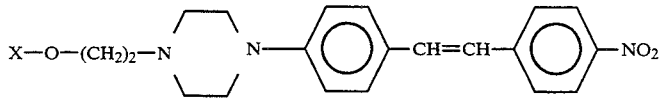
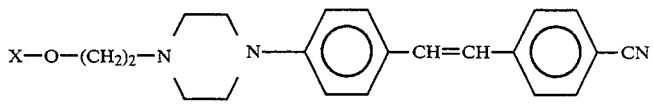
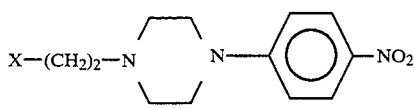

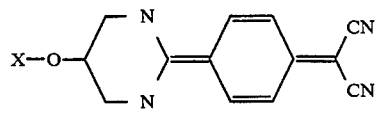

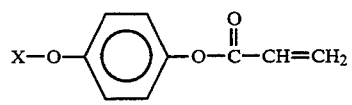

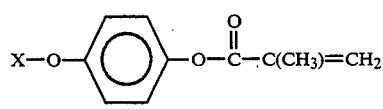

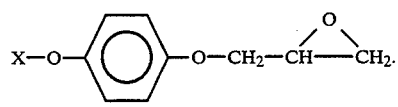

In which X has, for example, one of the meanings of

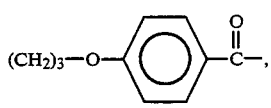

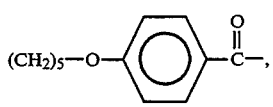

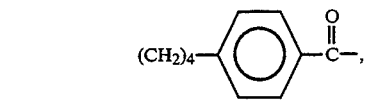

and Chol represents a cholesteryl radical, and

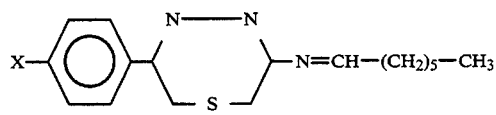

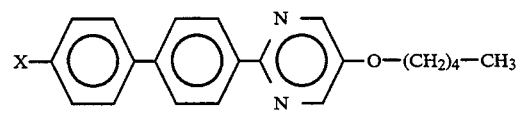

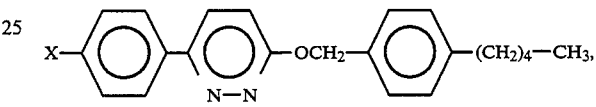

in which X has, for example, one of the meanings of (CH$_2$)$_6$—, (CH$_2$)$_6$—O—, (CH$_2$)$_4$— and (CH$_2$)$_4$—O—.

The radicals R$^1$ are preferably hydrocarbon radicals and substituted hydrocarbon radicals having from 1 to 6 carbon atoms.

Examples of R$^1$ radicals are all the substituted and unsubstituted radicals having from 1 to 6 carbon atoms mentioned for R$^4$.

The organosilsesquioxanes of this invention having at least one mesogenic side group, preferably have an average molecular weight of from 300 to 20,000 and more preferably from 1,000 to 10,000.

Examples of the organosilsesquioxanes of this invention having at least one mesogenic side group are

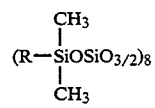

where

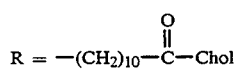

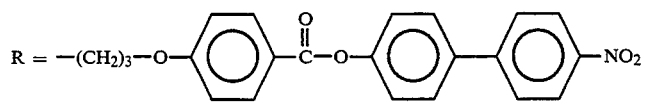

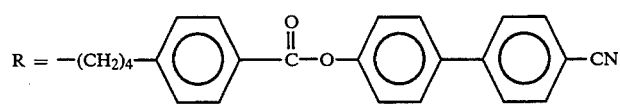

-continued
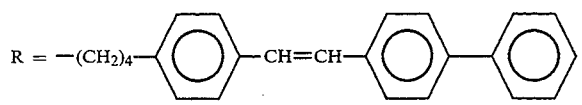
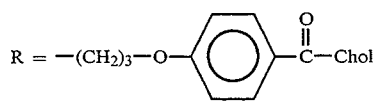 (50%)
and
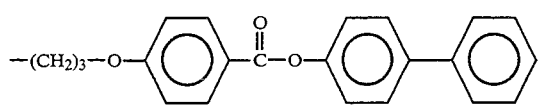 (50%)
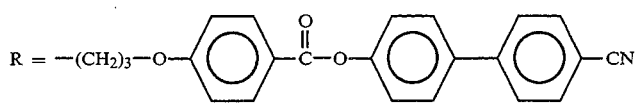 (50%)
and
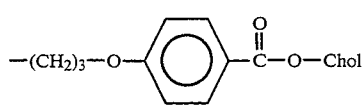 (50%)
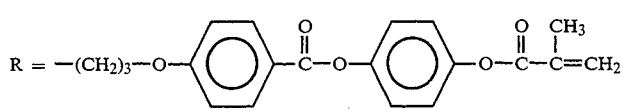 (30%)
and
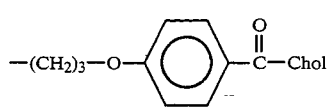 (70%)
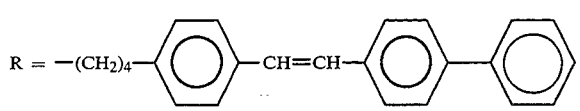 (50%)
and
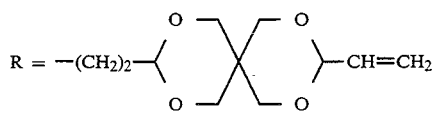 (5%)
and
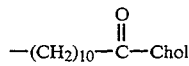 (95%)
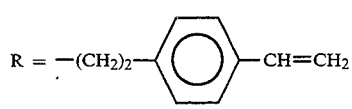 (30%)
and
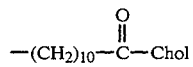 (70%)

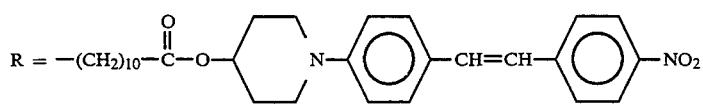 (50%)

and

 (50%)

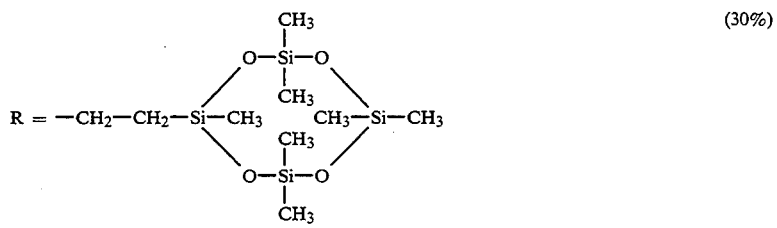 (30%)

and

 (70%)

and

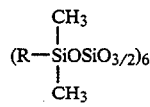

and

 (50%)

 (50%)

and

 (50%)

 (50%)

and

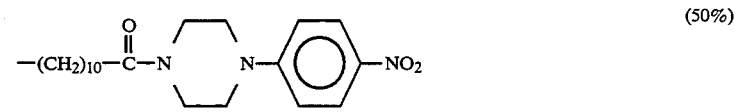 (50%)

in which Chol represents a cholesteryl radical and the percentage data are based on the total number of radicals R in the particular organosilsequioxane of this invention.

The organosilsesquioxanes of this invention having at least one mesogenic side group can be prepared by processes which are known per se. The organosilsesquioxanes according to the invention having at least one mesogenic side group are preferably prepared by reacting organosilsesquioxanes having at least one Si-bonded hydrogen atom, in particular those of the formula $$[R_{1-b}H_b(SiR^1{}_2O)_aSiO_{3/2}]_x \qquad (X)$$

in which R, $R^1$, a and x are the same as above and b can be the same or different and represents 0 or 1, with the proviso that the organosilsesquioxane of formula (X) contains at least one Si-bonded hydrogen atom and the radicals R have one of the meanings of $R^1$, with chiral or achiral mesogenic compounds which contain an aliphatic multiple bond, preferably a terminal aliphatic multiple bond, and more preferably those of the formulas $$H_2C=CH-C_{d-2}H_{e-4}-CR_2{}^2-C_dH_e-\overset{\overset{O}{\|}}{C}-Y \qquad (XI)$$

$$HC\equiv C-C_{d-2}H_{e-2}-CR_2{}^2-C_dH_e-\overset{\overset{O}{\|}}{C}-Y \qquad (XII)$$

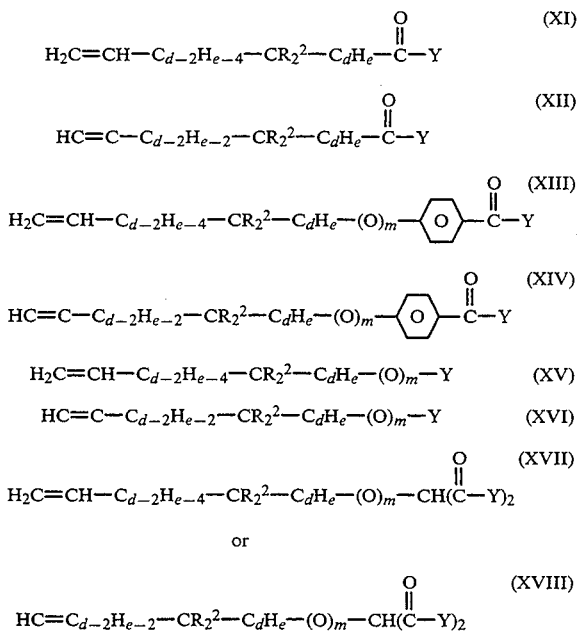

$$H_2C=CH-C_{d-2}H_{e-4}-CR_2{}^2-C_dH_e-(O)_m-Y \qquad (XV)$$

$$HC\equiv C-C_{d-2}H_{e-2}-CR_2{}^2-C_dH_e-(O)_m-Y \qquad (XVI)$$

$$H_2C=CH-C_{d-2}H_{e-4}-CR_2{}^2-C_dH_e-(O)_m-CH(\overset{\overset{O}{\|}}{C}-Y)_2 \qquad (XVII)$$

or $$HC\equiv C-C_{d-2}H_{e-2}-CR_2{}^2-C_dH_e-(O)_m-CH(\overset{\overset{O}{\|}}{C}-Y)_2 \qquad (XVIII)$$

in which $R^2$, d, e, m and Y are the same as above.

The organosilsesquioxanes which are employed in the process of this invention and have at least one Si-bonded hydrogen atom can be prepared by processes which are known per se, such as, for example, the works by M. G. Voronkov et al. Zhur. Obshchei Khimii 49 (7), page 1522 (1979); Dokl. Akad. Nauk. SSSR 281 (6), page 1374 (1985); ibid. 270 (4), page 888 (1983) and German Application No. P 38 37 397.1 (R. Weidner, Wacker-Chemie GmbH; date of application 3rd November and the corresponding U.S. application Ser. No. 416,073, now U.S. Pat. No. 5,047,492.

The organosilsesquioxane employed according to this invention having at least one Si-bonded hydrogen atom can be a single type or a mixture of at least two types of such organosilsesquioxanes having at least one Si-bonded hydrogen atom.

The chiral or achiral mesogenic compounds which are employed in the process of this invention and have an aliphatic multiple bond are commercially available products or can be prepared by methods described in organic chemistry. Reference may be made for example, to E. C. Taylor, J. S. Scotnicki, Synthesis (1981) 606.

The chiral or achiral mesogenic compounds which are employed according to this invention and contain an aliphatic multiple bond can be a single type or a mixture of at least two types of such compounds.

The reaction of organosilsesquioxanes having at least one Si-bonded hydrogen atom and chiral or achiral mesogenic compound which contains an aliphatic multiple bond is preferably carried out in the presence of a catalyst.

The catalysts employed in the process according to this invention can be the same as those which have been or could have been employed for adding Si-bonded hydrogen atoms to aliphatic multiple bonds. These are generally metals of sub-group 8 and inorganic and organic compounds thereof, in which platinum and compounds thereof are preferred.

Examples of such catalysts are finely divided elemental platinum supported on an inert carrier, such as active charcoal, $SiO_2$ or $Al_2O_3$, according to U.S. Pat. No. 2,970,150 (D. L. Bailey, Union Carbide Corporation; published on 31st January 1961), hexachloroplatinic acid according to U.S. Pat. No. 2,823,218 (J. L. Speier, Dow Corning Corporation; published on 11th February 1958) and chloroplatinates derived therefrom, platinum complexes of the type $L \cdot PtCl_2$, in which L denotes a linear or cyclic monoolefin, such as ethene, propene or cyclohexene, according to U.S. Pat. No. 3,159,601 and U.S. Pat. No. 3,159,662 (Bruce A. Ashby, General Electric Company; both published on 1st December 1964), platinum complexes of the type $L \cdot PtCl_2$, in which L represents a cyclic diolefin, such as 1,5-cyclooctadiene, norbornadiene and cyclopentadiene, according to Japanese Published Specification 79/76,529 and Japanese Published Specification 79/76,530 (Masatoshi Arai, Shin-Etsu Chemical Industry Co., Ltd.; both published on 19th June 1979) and U.S. Pat. No. 4,276,252 (G. Kreis, Wacker-Chemie GmbH, published on 30th June 1981), or represents a cyclic polyolefin, according to German Application No. P 39 06 514.6 (G. Wenski, Consortium für elektrochemische Industrie GmbH; date of application 1st March 1989), platinum-vinyl-siloxane complexes according to U.S. Pat. No. 3,814,730 (B. D. Karstedt, General Electric Company; published on 4th June 1974), and acetylacetonate complexes of platinum according to U.S. Pat. No. 4,177,341 (G. Kreis, Consortium für elektrochemische Industrie GmbH; published on 4th December 1979).

Because of their high activity, platinum complexes of the type $L \cdot PtCl_2$, in which L represents a cyclic di- or polyolefin and in particular dicyclopentadiene-platinum dichloride, are preferably employed in the process of this invention.

The catalyst employed in this invention can be a single type of catalyst or a mixture of at least two different types of such catalysts.

The amounts of catalysts employed in the process of this invention can be the same as those previously employed in known processes for adding Si-bonded hydrogen to an aliphatic multiple bond in the presence of a catalyst. These are preferably from 0.1 to 1000 ppm by weight, and more preferably from 2 to 400 ppm by weight, calculated as elemental platinum, and based on the total weight of the reaction mass.

The process of this invention can be carried out in the presence or in the absence of a solvent, the use of an organic solvent which is inert with respect to the reaction mass being preferred.

Examples of solvents are alcohols, such as methanol, ethanol, n-propanol, iso-propanol, n-, sec- and tert-butanol and 2-butanol; esters, such as methyl acetate, ethyl acetate, n- and iso-propyl acetate, n-, sec- and tert-butyl acetate, ethyl formate and diethyl carbonate; ethers, such as dioxane, tetrahydrofuran, diethyl ether, di-n-propyl ether, diisopropyl ether, di-n-butyl ether and anisole; chlorinated hydrocarbons, such as methylene chloride, chloroform, carbon tetrachloride, 1,2-dichloroethane, 1,1,1-trichloroethane, trichloroethylene, tetrachloroethylene and chlorobenzene; hydrocarbons, such as pentane, n-hexane, hexane isomer mixtures, cyclohexane, heptane, octane, wash benzine, petroleum ether, benzene, ethylbenzene, toluene and xylenes and ketones, such as acetone, methylethyl ketone and methyl isobutyl ketone, or mixtures of these solvents, in which toluene, methylene chloride and tetrahydrofuran are preferably employed.

The term solvent does not mean that all the reaction components are dissolved in the liquid. The reaction can also be carried out in a suspension or emulsion of one or more of the reactants.

The temperatures and pressures used in the process of this invention can be the same as those used in the previously known processes for adding Si-bonded hydrogen to an aliphatic multiple bond in the presence of a catalyst. These are preferably temperatures between 0° and 200° C. and pressures between 900 and 1,100 hPa, temperatures between 20° and 120° C. being preferred. If desired, higher or lower pressures can also be used.

The reaction time depends inter alia on the reaction temperature, the activity and the amount of catalyst. It is generally between 20 minutes and 24 hours.

The reaction mass in the process of this invention can of course also contain other substances in addition to the organosilsesquioxane having at least one Si-bonded hydrogen atom, chiral or achiral mesogenic compound, catalyst and if appropriate solvent.

The organosilsesquioxanes of this invention having at least one mesogenic side group have the advantage that, on the backbone, which is small because of their cage-like rigid structure, they can carry a high number of mesogenic groups and thereby provide a wide variation in the properties. This structure, which is approximately spherical and therefore predestined for good flow properties, also allows a good capacity for orientation in the liquid crystal phase even in cases of a high molecular weight.

The organosilsesquioxanes of this invention having at least one mesogenic side group furthermore have the advantage that they have relatively high glass transition points and in particular high clear points. Above their particular glass transition points, they form ductile films in the liquid crystal phase, and these can very easily be orientated just by mechanical treatment. This orientated state results in a transparent film which can be set by quenching to below the particular glass transition point. They can of course also be aligned by customary methods, such as by surface effects or electrical or magnetic fields.

The process of this invention has the advantage that the organosilsesquioxanes prepared according to this invention having at least one mesogenic side group can be adjusted in a relatively simple manner to form the properties desired. Thus, for example, by choosing the identical or different mesogenic radicals totalling up to x, x having the meaning described above, both the nature and width of the liquid crystal phase and the mechanical properties can be varied.

The organosilsesquioxanes of this invention having at least one mesogenic side group can be employed for all purposes for which compounds having liquid crystal properties have previously been used. Thus, they can be used, for example, in optoelectronics, non-linear optics, communications technology, computer technology, displays, optical switches, information stores and integrated circuits, as well as for medical uses. They are moreover also suitable for mechanical uses, such as, for example, in hydraulics.

The organosilsesquioxane of this invention having at least one mesogenic side group can moreover be allowed to crosslink in a manner which is known per se, such as, for example, under UV irradiation or the influence of agents which form free radicals, such as, for example, organic peroxides, if it contains at least one group which is capable of crosslinking. Organosilsesquioxanes of formula (I) in which the mesogenic radicals R contain groups which are capable of crosslinking, such as acrylic groups, methacrylic groups, epoxy groups, stilbene derivative and groups having terminal carbon-carbon multiple bonds necessary for the hydrosilylation reaction, are particularly suitable for the crosslinking. The crosslinking of the organosilsesquioxanes of this invention can be carried out after the process of the invention or during the process of the invention. Crosslinking during the process of this invention is obtained, in particular, if compounds having at least two terminal carbon-carbon multiple bonds, such as 1,4-divinylbenzene, 4,4'-divinylbiphenyl, 1,3-butadiene, 1,5-hexadiene and 3,9-divinyl-2,4,8,10-tetraoxaspiro-(5,5)undecane, are employed.

The three-dimensional structure of the organosilsesquioxanes of this invention also allows crosslinking in all three special directions with a high degree of crosslinking, depending on the choice of the R radicals.

The organosilsesquioxanes of this invention having at least one mesogenic side group can be employed as such. However, they can also be employed in combination with other components, such as, for example, cyclic and/or linear organopolysiloxanes, which optionally have liquid crystal properties.

In the following examples, all parts and percentages are by weight, unless otherwise specified. Unless stated otherwise, the following examples are carried out under the pressure of the surrounding atmosphere, that is to say, at about 1000 hPa, and at room temperature, that is at about 23° C., or at a temperature which is established when the reactants are brought together at room temperature without additional heating or cooling.

The glass transition temperatures and the clear points of the organosilsesquioxanes of this invention having at least one mesogenic side group are in each case determined by differential thermal analysis (DTA). The degree of purity is determined by gel permeation chromatography (GPC).

EXAMPLE 1

Preparation of octa(hydrogendimethylsiloxy)octasilsesquioxane of the formula $[HSi(CH_3)_2OSiO_{3/2}]_8$ About 1250 ml of 10% aqueous tetramethylammonium hydroxide solution are added to 82.2 g of precipitated silicic acid. After the mixture has been stirred at 25° C. for 16 hours and at 50° C. for 8 hours, a clear solution is obtained. The solution is concentrated to two thirds of its starting volume and the resulting tetramethylammonium silicate is crystallized at 4° C. About 359.5 g of tetramethylammonium silicate which still contains water are obtained. About 160 g of tetramethylammonium silicate are added in portions to a well-stirred mixture containing 400 ml of water, 1000 ml of isopropanol, 1500 ml (1136 g) of 1,1,3,3-tetramethyldisiloxane (obtained under the name "HSi2" from Wacker-Chemie GmbH, D-8000 Munich) and 200 ml of 10% hydrochloric acid and the reaction mixture is then stirred at room temperature for 4 hours. The phases are then separated and the organic phase is washed with water until neutral, dried over sodium sulfate and evaporated completely. The residue is recrystallized from acetone. About 52.0 g of octa(hydrogendimethylsiloxy)octasilsesquioxane are obtained.

About 0.08 ml of a 1% solution of dicyclopentadiene-platinum dichloride in methylene chloride, which is prepared by processes known from the literature, such as, for example, J. Chatt, L. M. Vallarino, L. M. Venanzi, J. Chem. Soc. (London) (1957) 2496-505 and H. C. Clark, L. E. Manzer, J. Organometal, Chem. 59 (1973) 411–28, is added to a mixture containing 1.0 g of the octa(hydrogendimethysiloxy)octasilsesquioxane described above, 1.3 g of biphenyl-4-allyloxybenzoate of the structural formula

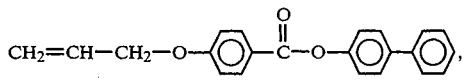

2.2 g of cholesteryl-4-allyloxybenzoate and 12 ml of anhydrous toluene and the mixture thus obtained is heated at the boiling point under reflux for 90 minutes. The mixture is filtered over a short column filled with silica gel to remove the fine platinum-containing precipitate. The solvents are then distilled off under reduced pressure and the residue is dissolved in tetrahydrofuran. The reaction product is precipitated by addition of ethanol, filtered off and dried under reduced pressure at a temperature of 60° C. About 3.5 g of a colorless solid which, according to GPC has a purity of 100%, are obtained. This substance is applied to a microscope slide, covered with a cover slide and heated slowly. From 110° C., the substance can be orientated by gentle pressure and mechanical shearing. The transparent film thus obtained shows a smectic A phase having a crystalline content from room temperature to 127° C. and a smectic A phase from 127° C. up to the clear range between 200° and 220° C.

EXAMPLE 2

About 0.02 ml of the 1% dicyclopentadieneplatinum dichloride solution described in Example 1 is added to a mixture containing 0.2 g of the octa(hydrogendimethylsiloxy) octasilsesquioxane described in Example 1, 0.9 g of cholesteryl-10-undecanoate and 3 ml of anhydrous methylene chloride. The resultant mixture is processed in the same manner as described in Example 1. About 0.6 g of a colorless solid which, according to GPC, has a purity of 100% is obtained. The transparent film obtained after the preparation described in Example 1 (shearing from 100° C.) shows an unstable smectic A phase, which tends to crystallize, from room temperature to 108° C. and a pure smectic A phase from 108° C. to the clear point of 160° C. The glass transition point is 50° C.

EXAMPLE 3

About 0.04 ml of the dicyclopentadiene-platinum dichloride solution described in Example 1 is added to a mixture containing 0.5 g of the octa(hydrogendimethylsiloxy) octasilsesquioxane described in Example 1, 1.4 g of 4'-cyanobiphenyl-4-allyloxybenzoate of the structural formula

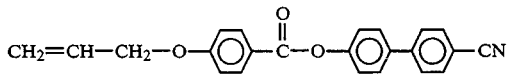

and 5 ml of anhydrous toluene. The resultant mixture is processed in accordance with the procedure described in Example 1. About 0.8 g of a colorless solid which, according to GPC, has a purity of 100% is obtained. The transparent film obtained after the preparation described in Example 1 (shearing from 130° C.) shows a smectic B phase having a crystalline content from room temperature up to the range between 118° and 135° C. and a smectic A phase above this range up to the clear range above 300° C. The glass transition point is 102° C.

EXAMPLE 4

About 0.04 ml of the dicyclopentadiene-platinum dichloride solution described in Example 1 is added to a mixture containing 0.5 g of the octa(hydrogendimethylsiloxy) octasilsesquioxane described in Example 1, 1.1 g of cholesteryl-4-allyloxybenzoate, 0.7 g of 4'-nitrobiphenyl 4-allyloxybenzoate of the structural formula

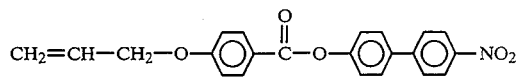

and 6 ml of anhydrous toluene. The resultant mixture is processed in the manner as described in Example 1. About 0.5 g of a colorless solid which, according to GPC, has a purity of 99.5% is obtained. The transparent film obtained after the preparation described in Example 1 (shearing at 140° C.) shows a smectic A phase having a crystalline content from room temperature up to the range between 105° and 170° C. and a smectic A phase above this range up to the clear range about 300° C. The glass transition point is 60° C.,

EXAMPLE 5

About 2.42 g of hexamethyldisilazane (commercially available from Wacker-Chemie GmbH, D-8000 Munich) are added dropwise to a mixture containing 5.75 g of 4-hydroxyphenyl-4-allyloxybenzoate (which can be prepared in accordance with German Application No. P 38 30 592; F.-H Kreuzer, Consortium für elektrochemische Industrie, applied for on 8th September 1988) and 20 ml of dry toluene at a temperature of 90° C. under an argon atmosphere, and the mixture is then heated at the boiling point under reflux for 1 hour. The volatile constituents are distilled off, the residue is dissolved in 40 ml of anhydrous methylene chloride, together with 27.2 g of cholesteryl-4-allyloxybenzoate and 9.8 mg of the dicyclopentadiene-platinum dichloride described in Example 1, at a temperature of 60° C. and 10 g of the octa(hydrogengen-dimethylsiloxy)octasilsesquioxane described in Example 1 are added. The mixture thus obtained is heated at the boiling point under reflux for 1 hour and the methylene chloride is then distilled off and replaced by toluene. The mixture thus obtained is heated to the boiling point and a solution of 0.4 g of concentrated hydrochloric acid in 60 ml of ethanol is added dropwise over a period of 1 hour, the solvent mixture being continuously distilled off and the trimethylsilyl protective group being split off. After the solvent has been stripped off, 7 g of a colorless solid are obtained and are dissolved in 150 ml of toluene, and the solution is heated at 100° C. for 1 hour with 0.83 g of methacrylic anhydride and 0.3 g of 4-toluenesulfonic acid. After cooling, the methacrylated product, which is capable of crosslinking, is reprecipitated from toluene/methanol. About 6 g of a slightly grey solid which is amorphous at room temperature and must be stored in the dark because of its ease of crosslinking by UV light are obtained.

EXAMPLE 6

Preparation of deca(hydrogendimethylsiloxy)decasilsesquioxane of the formula $[HSi(CH_3)_2OSiO_{3/2}]_{10}$ About 490 g (500 ml) of 40% aqueous tetra-n-butylammonium hydroxide solution (commercially available from Fluka, D-7910 Neu-Ulm) are diluted with 700 ml of water, and then 223.2 g of tetraethoxysilane are added slowly. The mixture is then stirred at room temperature for 24 hours. It is then concentrated to 64.9% of the original total volume by distillation and the solution is crystallized at 4° C. About 50 g of this tetra-n-butylammonium silicate are slowly added to a mixture containing 250 ml (189.3 g) of 1,1,3,3-tetramethyldisiloxane (obtained under the name "HSi2" from Wacker-Chemie GmbH, D-8000 Munich), 130 ml (112.2 g) of dimethylchlorosilane and 50 ml of isopropanol at 5° C. The mixture is then stirred at room temperature for 6.5 hours. About 300 ml of ice-water are subsequently added, the organic phase is washed until neutral, then dried over sodium sulfate and filtered off and the solvent is removed at 60° C. at 1500 Pa. About 8.5 g of a viscous crystalline mass remains. Crystallization from a little 1,1,3,3-tetramethyldisiloxane gives 1.86 g of deca(hydrogendimethylsiloxy)decasilsesquioxane.

About 0.08 ml of the dicyclopentadiene-platinum dichloride solution described in Example 1 is added to a solution, boiling under reflux, containing 4.3 g of cholesteryl 10-undecanoate in 8 ml of dry toluene and a solution containing 0.5 g of the deca(hydrogendimethylsiloxy) decasilsesquioxane described above in 5 ml of dry toluene is added dropwise to the resulting mixture over a period of 2 hours. The mixture is then boiled under reflux for an additional hour. It is filtered through a short column filled with silica gel to remove the finely divided platinum-containing precipitate. The crude product is precipitated from the toluene solution by addition of 50 ml of ethanol and separated off by filtration. After several further operations of dissolving in toluene, precipitating with ethanol and subsequent filtration and after drying at 90° C. under reduced pressure, about 1.5 g of a colorless substance are obtained which, according to GPC, is 100% pure. The completely substituted structure is confirmed by a molecular weight of about 6800, obtained from the GPC, the IR spectrum (Si-H band no longer present) and by the $^{29}$Si-NMR spectrum (signals at 11.99 and $-110.0$ ppm). The substance is introduced onto a microscope slide, covered with a cover slide and heated slowly. A transparent film can be produced from 128° C. by mechanical shearing. This shows a smectic B phase having a crystalline content from room temperature to 50° C. and a pure smectic B phase above this temperature to 80° C., and a smectic A phase is present above 88° C. up to the clear point at 165° C. The glass transition point of the compound is 51° C.

EXAMPLE 7 a) Synthesis of 4-buten-3-ylbenzyl chloride

A Grignard solution prepared from 92 g of magnesium filings and 150.8 ml of allyl chloride in 1.2 liter of anhydrous tetrahydrofuran is slowly added at 15° C. dropwise to a solution containing 227.0 g of α,α'-dichloro-p-xylene in 1 liter of anhydrous tetrahydrofuran and the mixture is stirred at room temperature for 14 hours. The reaction mixture is then poured into dilute hydrochloric acid (pH=4–5), the organic phase is separated off, the aqueous phase is extracted several times by shaking with methyl tert-butyl ether (obtained under the name Driveron-S from the Hüls AG Chemical Works, D-4370 Marl) and the combined organic phases are dried over sodium sulfate. To remove any magnesium salts, the organic phase is filtered through a column filled with Tonsil and dried again over sodium sulfate and the solvent is distilled off. The residue is suspended in cold n-heptane, the heptane phase is filtered, allowed to stand in a refrigerator for several hours and filtered again and the solvent is stripped off. About 27 g of 4-buten-3-ylbenzylchloride are obtained as a yellowish oil.

b) Synthesis of 4-buten-3-ylbenzyl diethyl phosphonate

About 112.7 g of the 4-buten-3-ylbenzyl chloride described above are slowly added dropwise to 121.3 ml of triethyl phosphite at 90° C. The temperature is then kept at 110° C. for 3 hours, at 130° C. for 8 hours and finally at 150° C. for 3 hours. After distillation through a 15 cm Vigreux column under $6 \times 10^{-3}$ mm Hg, 140.03 g of 4-buten-3-ylbenzyl diethyl phosphonate are obtained between 127° C. and 130° C.

c) Synthesis of 4-phenyl-4'-buten-3-ylstilbene

A mixture containing 45.2 g of 4-biphenylylaldehyde (commercially available from Janssen Chimica, D-4054 Nettetal) and 70.0 g of the 4-buten-3-ylbenzyl diethyl phosphonate described above is slowly added dropwise to a mixture, cooled to 0° C., containing 29.2 g of potassium tert-butyl-alcoholate, 0.6 g of potassium iodide and 2.4 g of crown ether 18-Cr-6, while stirring vigorously. During the exothermic reaction, a colorless precipitate forms immediately from the red solution. After stirring at room temperature for 2 hours, the reaction mixture is left to stand for an additional 24 hours. The precipitate is then filtered off and recrystallized from ethanol. About 65 g of slightly greenish crystals having a melting point of 214° C. are obtained. The structure is confirmed by the $^1$H-NMR.

About 0.08 ml of the 1% solution, described in Example 1, of dicyclopentadiene-platinum dichloride in methylene chloride is added to a solution containing 3.0 g of the 4-phenyl-4'-buten-3-ylstilbene described above and 1.1 g of the octa(hydrogendimethylsiloxy)octasilsesquioxane described in Example 1 in 21 ml of anhydrous toluene and the mixture thus obtained is heated at the boiling point under reflux for 3 hours. The colorless, very slightly soluble product which has precipitated is filtered off with suction, extracted by stirring with tetrahydrofuran and dried at 60° C. under reduced pressure. The yield is 3.5 g. The substance is highly fluorescent under UV light and crystalline at 248° C. It moreover has a smectic A phase (in which the mechanical orientation takes place), which has isotropic portions from 286° C. The clear point is about 300° C.

EXAMPLE 8

About 0.14 ml of the 1% solution, described in Example 1, of dicyclopentadiene-platinum dichloride in methylene chloride is added to a solution containing 0.5 g of 4,4-divinylbenzene (commercially available from Aldrich-Chemie GmbH & Co. KG, D-7924 Steinheim), 5..0 g of cholesteryl-10-undecanoate and 2.1 g of the octa(hydrogendimethylsiloxy) octasilsesquioxane described in Example 1 in 20 ml of anhydrous toluene and the mixture thus obtained is heated at the boiling point under reflux for 3 hours. It is filtered through a short column filled with silica gel to remove the finely divided platinum-containing precipitates. The solvent is then distilled off under reduced pressure and the crude product is dissolved in tetrahydrofuran, reprecipitated twice with ethanol and dried at 60° C. under reduced pressure. About 5.2 g of a colorless product which, according to GPC, is 100% pure are obtained. After orientation at 70° C., this product forms a colorless film which shows a nematic phase from room temperature up to the clear range between 92° and 130° C. The glass transition point is 20° C.

EXAMPLE 9

About 0.09 ml of the 1% solutions described in Example 1, of dicyclopentadiene-platinum dichloride in methylene chloride is added to a solution containing 0.5 g of 3,9-divinyl-2,4,8,10-tetraoxaspiro(5.5)undecane (obtained from Aldrich-Chemie GmbH & Co. KG, D-7924 Steinheim) of the formula

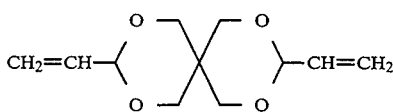

3.0 g of cholesteryl-10-undecanoate and 1.2 g of the octa(hydrogendimethylsiloxy)octasilsesquioxane described in Example 1 in 13 ml of anhydrous toluene and the mixture thus obtained is heated at 70° C. for 90 minutes. The product which precipitates during this procedure is dissolved by addition of tetrahydrofuran and the solution is filtered through a short column filled with Tonsil to remove the finely divided platinum-containing precipitates. The solvent is then stripped off, the colorless viscous residue is taken up in tetrahydrofuran and the product is precipitated with ethanol. This reprecipitation is repeated twice more. After drying at 90° C. under reduced pressure, 3.2 g of a colorless solid are obtained. GPC shows that, in addition to monomers, the dimers are also formed as a crosslinking product in a ratio of 1:1. Preparation and orientation of the sample at 90° C. results in a clear film which has a smectic A phase having a crystalline content from room temperature to 90° C. and a pure smectic A phase above this temperature up to the clear range between 146° and 157° C. The glass transition point is 36° C.

EXAMPLE 10

Preparation of hexa(hydrogendimethylsiloxy)hexasilsesquioxane of the formula $[HSi(CH_3)_2OSi_{3/2}]_6$.

About 412 g (400 ml) of 40% aqueous tetraethylammonium hydroxide solution (commercially available from Fluka, D-7910 Neu-Ulm) is diluted with 200 ml of water, and 225 g of tetraethoxysilane are slowly added. The mixture is then stirred at room temperature for 24 hours. The mixture is then concentrated to 45.2% of the original weight by distillation and the solution is crystallized at 4° C. About 22 g of this tetraethylammonium silicate are added to a mixture, cooled to 5° C., containing 80 ml (60.6 g) of 1,1,3,3-tetramethyldisiloxane (obtained under the name "HSi2" from Wacker-Chemie GmbH, D-8000 Munich), 80 ml (69.1 g of dimethylchlorosilane (commercially available under the name "M2" from Wacker-Chemie GmbH, D-8000 Munich) and 160 ml of dimethylformamide over a period of 20 minutes. During this procedure the temperature rises from 5° C. to 15° C. The mixture is then stirred at 5° C. for 1 hour. About 200 ml of ice-water are then added, the organic phase is washed with water until neutral, dried over sodium sulfate and filtered and the solvent is distilled off at 60° C. at 1500 Pa. A clear viscose liquid remains, and on cooling, 1.63 g of crystals precipitate out, which can be filtered off.

About 0.09 ml of the 1% solution., described in Example 1, of dicyclopentadiene-platinum dichloride in methylene chloride is added to a solution containing 4.35 g of cholesteryl-10-undecanoate and 0.5 g of the hexa(hydrogen-dimethylsiloxy)hexasilsesquioxane described above in 13 ml of anhydrous toluene and the mixture thus obtained is stirred at room temperature for 14 hours. It is filtered through a short column filled with silica gel to remove the finely divided platinum-containing precipitates. The solvent is then distilled off under reduced pressure and the crude product is dissolved in tetrahydrofuran, reprecipitated with ethanol and dried at 60° C. under reduced pressure. About 1.3 g of a colorless solid which, according to GPC, is 100% pure are obtained. Sample preparation results, by mechanical shearing from 77° C., in a transparent film which shows a smectic A phase having a crystalline content from room temperature to 37° C. and a pure smectic A phase above this temperature up to the clear range between 136° and 148° C. The glass transition point is 30° C.

What is claimed is:

1. A compound having the general formula $$[R(SiR^1{}_2O)_a SiO_{3/2}]_x$$

in which x is 4, 6, 8, 10 or 12, a is an integer of from 1 to 10, $R^1$ is a monovalent organic radical and R is a radical selected from the group consisting of a chiral mesogenic radical and achiral mesogenic radical, with the proviso that up to $x-1$ of the radicals R are the same as $R^1$.

2. The organosilsesquioxane of claim 1, in which R represents a radical selected from the group consisting of the formula

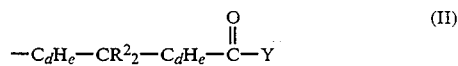  (II)

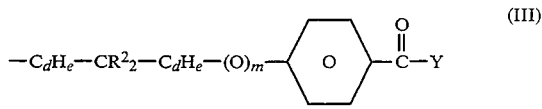  (III)

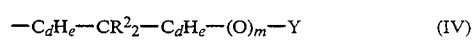  (IV)

and

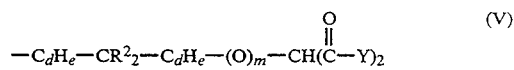  (V)

in which $R^2$ is a radical selected from the group consisting of a hydrogen atom, cyano group, hydroxyl group, halogen atom and alkyl group having from 1 to 4 carbon atoms, d is an integer of from 0 to 12, e is an integer of from 0 to 24, m is 0 or 1 and Y is selected from the group consisting of a cholesteryl radical and a radical selected from the group consisting of the formulas

  (VI)

-continued

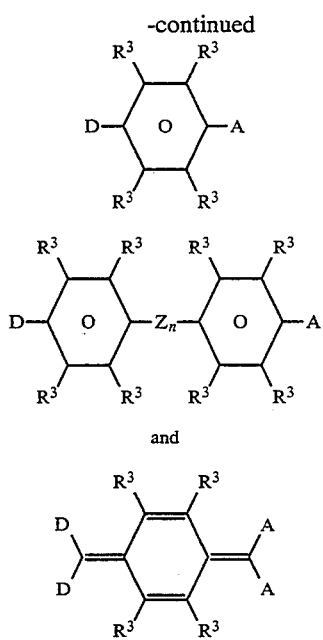

in which P is a radical selected from the group consisting of an oxygen atom, a sulfur atom, —$C_dH_e$—, where d and e are the same as above, and an N-alkylamino radical, v is an integer of from 0 to 12, E is a radical selected from the group consisting of —$CH_2$—$CH_2$—, —$CH_2O$—, —$OCH_2$—, —COS— and a conjugated multiple bond system between identical or different atoms, r is an integer of from 0 to 8, c is an integer of from 1 to 5, f is an integer of from 1 to 5, $R^4$ is a radical selected from the group consisting of a hydrogen atom, halogen atom, hydroxyl group, nitro group, amino group, cyano group, chiral hydrocarbon, achiral hydrocarbon, hydrocarbonoxy, ester, acyl and acyloxy radicals, which can optionally be substituted, and B is a divalent cyclic radical selected from the group consisting of cyclic hydrocarbons and heterocyclic radicals, with the proviso that these radicals can be substituted by a radical selected from the group consisting of a halogen atom, hydroxyl group, nitro group, amino group, cyano group, chiral hydrocarbon, achiral hydrocarbon, hydrocarbonoxy, ester, acyl and acyloxy groups, which can optionally be substituted, $R^3$ is the same as $R^4$, A is an electron-attracting radical, D is an electron-repelling radical, Z is a conjugated multiple bond system between identical or different atoms, and n is an integer of from 0 to 8, with the proviso that formulas (VII), (VIII) and (IX) represent monovalent radicals formed by removal of one hydrogen.

3. The organosilsesquioxane of claim 2, in which Y is a cholesteryl radical.

4. The organosilsesquioxane of claim 2, in which Y represents a radical of the general formula —$P_v$—$(B_f$—$E_r)_c$—$R^4$     (VI)

in which P is a radical selected from the group consisting of an oxygen atom, a sulfur atom, —$C_dH_e$—, where d is an integer of from 0 to 12 and e is an integer of from 0 to 24, and an N-alkylamino radical, v is an integer of from 0 to 12, E is a radical selected from the group consisting of —$CH_2CH_2$—, —$CH_2O$—, —$OCH_2$—, —COS— and a conjugated multiple bond system between identical or different atoms, r is an integer of from 0 to 8, c is an integer of from 1 to 5, f is an integer of from 1 to 5, $R^4$ is a radical selected from the group consisting of a hydrogen atom, halogen atom, hydroxyl group, nitro group, amino group, cyano group, chiral hydrocarbon, achiral hydrocarbon, hydrocarbonoxy, ester, acyl and acyloxy radicals, which can optionally be substituted, and B is a divalent cyclic radical selected from the group consisting of cyclic hydrocarbons and heterocyclic radicals, with the proviso that these radicals can be substituted by a radical selected from the group consisting of a halogen atom, hydroxyl group, nitro group, amino group, cyano group, chiral hydrocarbon, achiral hydrocarbon, hydrocarbonoxy, ester, acyl and acyloxy groups, which can optionally be substituted.

5. The organosilsesquioxane of claim 2, in which Y is a radical of the formula

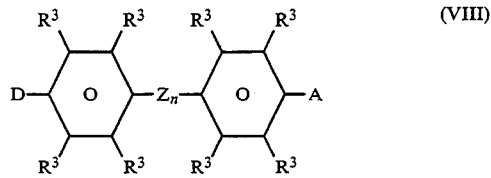

in which $R^3$ is a radical selected from the group consisting of a hydrogen atom, halogen atom, hydroxyl group, nitro group, amino group, cyano group, chiral hydrocarbon, achiral hydrocarbon, hydrocarbonoxy, ester, acyl and acyloxy radicals, which can optionally be substituted, A is an electron-attracting radical and D is an electron-repelling radical.

6. The organosilsesquioxane of claim 2, in which Y is a radical of the formula

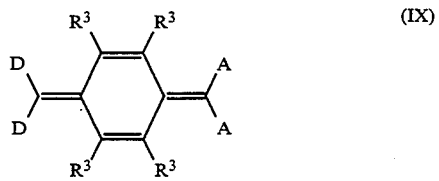

in which $R^3$ is a radical selected from the group consisting of a hydrogen atom, halogen atom, hydroxyl group, nitro group, amino group, cyano group, chiral hydrocarbon, achiral hydrocarbon, hydrocarbonoxy, ester, acyl and acyloxy radicals, which can optionally be substituted, A is an electron-attracting radical, D is an electron-repelling radical, Z is a conjugated multiple bond system between identical or different atoms, and n is an integer of from 0 to 8.

7. The organosilsesquioxane of claim 2, in which Y is a radical of the formula

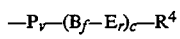

in which $R^3$ is a radical selected from the group consisting of a hydrogen atom, halogen atom, hydroxyl group, nitro group, amino group, cyano group, chiral hydrocarbon, achiral hydrocarbon, hydrocarbonoxy, ester, acyl and acyloxy radicals, which can optionally be substituted, A is an electron-attracting radical and D is an electron-repelling radical.

* * * * *